United States Patent
Kanesaka

(10) Patent No.: US 6,796,948 B2
(45) Date of Patent: Sep. 28, 2004

(54) GUIDE WIRE INSTALLATION DEVICE FOR CATHETER

(75) Inventor: Nozomu Kanesaka, Old Tappan, NJ (US)

(73) Assignee: Bolton Medical Inc., Fair Lawn, NJ (US)

(*) Notice: Subject to any disclaimer, the term of this patent is extended or adjusted under 35 U.S.C. 154(b) by 387 days.

(21) Appl. No.: 10/081,037

(22) Filed: Feb. 21, 2002

(65) Prior Publication Data

US 2003/0158561 A1 Aug. 21, 2003

(51) Int. Cl.[7] .................................................. A61F 5/00
(52) U.S. Cl. ........................................ 600/585; 600/434
(58) Field of Search ................................. 600/434, 470, 600/374, 381, 433, 585; 606/108

(56) References Cited

U.S. PATENT DOCUMENTS 5,255,690 A * 10/1993 Keith et al. .................. 600/585
5,357,961 A * 10/1994 Fields et al. ................. 600/435
5,454,785 A * 10/1995 Smith .......................... 600/585

* cited by examiner

Primary Examiner—Kevin T. Truong
(74) Attorney, Agent, or Firm—Laurence A. Greenberg; Werner H. Stemer; Gregory L. Mayback

(57) ABSTRACT

A guide wire installation device for a catheter includes a pair of elongated main sections arranged to face each other. Each main section includes a gripping portion at one side, and a holding portion at the other side thereof. The holding portion has first and second grooves communicating with each other. The first groove has a size greater than that of the second groove. When the holding portions abut against each other, a hollow portion is formed by the first grooves, and a receiving hole communicating with the hollow portion is formed by the second grooves. The catheter can be held at the receiving hole, so that the guide wire or syringe for saline can be inserted through the hollow portion.

6 Claims, 1 Drawing Sheet

GUIDE WIRE INSTALLATION DEVICE FOR CATHETER

BACKGROUND OF THE INVENTION AND RELATED ART STATEMENT

The present invention relates to a guide wire installation device for a catheter in installing the catheter onto a guide wire in a percutaneous transluminal coronary angioplasty (PTCA) procedure.

A catheter, such as balloon catheter, has been widely used for vascularization of a coronary artery or delivering and placing a stent in the coronary artery or other portions. In this case, a catheter is delivered into the artery through a guide wire already placed in the artery to enlarge a stenosis, i.e. constriction in the coronary artery, or deliver and place the stent.

In particular, in delivering the catheter into the blood vessel, at first, a through hole for the guide wire in the catheter must be filled with saline to prevent air from entering into the blood vessel, and then, the guide wire is inserted into the through hole of the catheter. Thereafter, the catheter is inserted into the blood vessel through the guide wire.

In this respect, generally, the guide wire has the diameter of only 0.014 inches, and the catheter tip has an opening of a through hole of 0.015 inches. Therefore, it is difficult to enter a needle of a syringe into the opening of the catheter to provide saline into the catheter, and then, to enter the guide wire into the opening of the catheter.

Especially, it is desirable to quickly prepare the catheter for treatment to shorten the operation time. Also, a catheter used for one procedure may be exchanged with another catheter, and in this case, the catheter must be prepared as quickly as possible. However, there is no special device to help using the catheter in receiving saline and installing the guide wire.

The present invention has been made in view of the above problems, and an object of the invention is to provide a guide wire installation device for a catheter for help inserting the guide wire into a through hole of the catheter.

Another object of the invention is to provide a guide wire installation device as stated above, which can also be used in providing saline into the through hole of the catheter.

A further object of the invention is to provide a guide wire installation device as stated above, which can also be used in holding a catheter in a small size, as a clip.

Further objects and advantages of the invention will be apparent from the following description of the invention.

SUMMARY OF THE INVENTION

In accordance with the invention, a guide wire installation device for a catheter is formed a pair of elongated main sections arranged to face each other. Each main section includes a gripping portion at one side, and a holding portion at the other side thereof arranged to slightly incline relative to the gripping portion. The holding portion has first and second grooves communicating with each other and extending in a direction to cross with a longitudinal direction of the main section. The first groove has a size greater than that of the second groove.

The guide wire installation device also includes a connecting portion located between the holding portion and the gripping portion for connecting the elongated main sections together, and means for holding the holding portions to abut against each other. When the holding portions abut against each other, a hollow or introducing portion is formed by the first grooves, and a receiving hole communicating with the hollow portion is formed by the second grooves.

In the invention, the holding portions are generally closed by the means for holding the holding portions to form the hollow portion and the receiving hole. When necessary, the gripping portions are pressed to each other, so that the holding portions open around the connecting portion.

The guide wire installation device of the invention is used to help filling saline into a through hole of a catheter and installing the guide wire into the through hole filled with saline.

In filling saline into the through hole of the catheter, an end of the catheter is held in the receiving hole, i.e. between the second grooves. In this case, the end of the catheter may be inserted into the receiving hole, or the gripping portions may be pushed to open the holding portions, and after placing the end of the catheter into the second groove, the holding portions may be closed. Thereafter, a needle attached to a syringe with saline therein is inserted into the through hole of the catheter through the hollow portion formed by the first grooves greater in diameter than the through hole of the catheter. Then, saline is injected into the through hole of the catheter by the syringe. Since the needle can be easily inserted into the through hole of the catheter, saline can be easily supplied to the through hole of the catheter.

When a guide wire is inserted into the through hole of the catheter, the needle for the syringe is removed after filling saline into the through hole, and then, the guide wire is inserted into the through hole through the hollow portion. Since the size of the hollow portion is greater than that of the through hole, the guide wire can be easily inserted into the through hole of the catheter. After the guide wire is inserted into the catheter, the gripping portions are pushed toward each other to open the holding portions. Accordingly, the guide wire installation device can be easily removed laterally from the guide wire or catheter. Thereafter, the catheter is inserted into the blood vessel along the guide wire.

Preferably, the first groove has a tapering surface extending to the second groove to form a conical shape when the holding portions abut against each other. In this structure, the first grooves form a funnel shape, so that once the needle or guide wire is inserted into the hollow portion, the needle or guide wire can be lead to the through hole of the catheter held in the receiving hole.

Preferably, the second groove has step portions with different sizes to form different diameter portions when the holding portions abut against each other. The diameters of the different diameter portions gradually increase in a direction away from the first groove. Thus, the guide wire installation device can be used for different catheters with different tip sizes.

The means for holding the holding portions may be an elongated member located between the gripping portions. The elongated member may provide pressure outwardly to the gripping portions to urge and close the holding portions, or simply support the gripping portions to close the holding portions. The main sections, elongated curved member and connecting portion may be integrally formed together by resin.

The main section may further include a third groove between the holding portion and the connecting portion to form a clip for a catheter when the holding portions abut against each other. In this case, the elongated catheter can be bent to have loops, which are held between the third grooves.

DETAILED DESCRIPTION OF PREFERRED EMBODIMENTS

Figure 1:
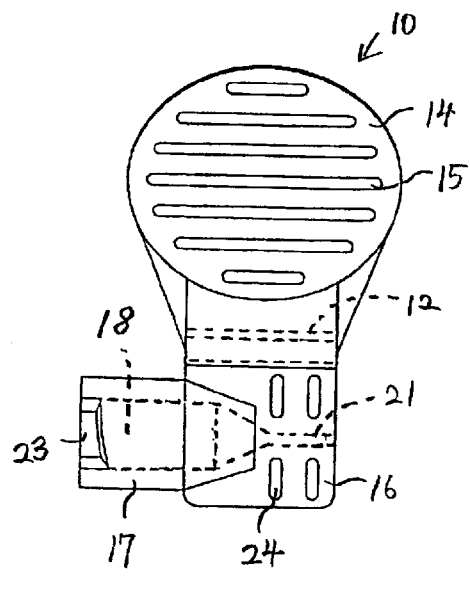
FIG. 1 is a front view showing a guide wire installation device of the present invention.
Figure 2:
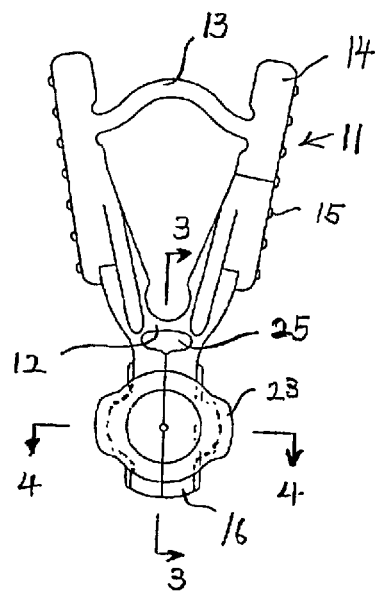
FIG. 2 is a side view of the guide wire installation device of the invention.
Figure 3:
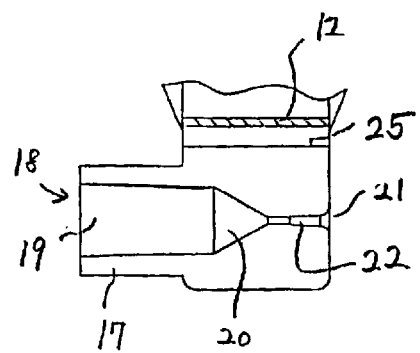
FIG. 3 is a sectional view taken along line 3—3 in FIG. 2.
Figure 4:
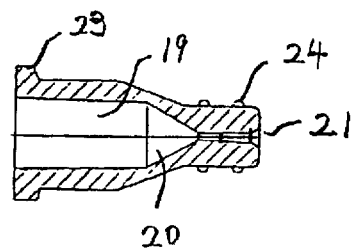
FIG. 4 is a sectional view taken along line 4—4 in FIG. 2.

Hereinafter, embodiments of the present invention will be explained with reference to the accompanying drawings.

A guide wire installation device 10 of the invention is used in installing a catheter onto a guide wire for PTCA procedure, delivering a stent and so on. Namely, in the guide wire installation device, saline can be easily filled in a through hole of a catheter by a syringe in order to prevent air from entering into a blood vessel when the catheter is delivered into the blood vessel, and the guide wire can be easily entered into the through hole of the catheter.

The guide wire installation device 10 is formed of a pair of main bodies 11 connected at a connecting portion or support 12 and a curved spring portion 13. The installation device 10 is integrally connected together by resin.

Each main body 11 includes a gripping portion 14 with ribs 15 at one end, and a holding portion 16 at the other end. The holding portion 16 is inclined relative to the gripping portion 14 at the connecting portion 12. The holding portion 16 includes a protrusion 17 extending substantially perpendicularly to a longitudinal direction of the main body 11. The holding portion 16 also includes a first or large groove 18 having a semi-cylindrical portion 19 and a semi-conical portion 20, and a second or small groove 21 with steps 22 communicating with the semi-conical portion 20. The sizes of the steps 22 gradually increase outwardly from the large groove 18 in order to receive tips of catheters with different sizes.

When the holding portions 16 of the main bodies 11 abut against each other, the large grooves 18 form a hollow or introducing portion having a cylindrical portion and a conical portion, and the small grooves 21 form a receiving hole. The cylindrical portion is formed by the semi-cylindrical portions 19, and the conical portion is formed by the semi-conical portions 20.

The protrusion 17 includes a projection 23 extending outwardly therefrom. Also, ribs 24 are formed on the outer surface of the holding portion 16. The protrusions 17 with the projections 23 are formed to hold the installation device by fingers in manipulating the installation device 10.

Each main body 11 further includes a groove 25 near the connecting portion 12. When the holding portions 16 abut against each other, the grooves 25 form a holding hole, which can be used to hold the loops of the catheter when turning or bending the catheter. Therefore, the installation device 10 can be used to hold the catheter in a small size.

The connecting portion 12 connects the main bodies 11 together, and is made to bend when the gripping portions 11 are pushed toward each other. Instead of the connecting portion 12, the main bodies 11 may be formed separately and are urged toward each other so that the holding portions 16 abut against each other. The curved spring portion 13 operates to provide an outward force to the gripping portions 11, so that the holding portions 16 abut against each other.

In this structure, the spring portion 13 pushes the gripping portions 11 outwardly. However, the spring portion 13 may be formed to simply hold the holding portions 16 to abut against each other without applying spring force thereto. For this purpose, the portion 13 may have several slits to allow the portion 13 to bend toward the connecting portion 12 when the gripping portions 11 are pushed, so that the holding portions 16 can be opened.

The guide wire installation device 10 of the invention as explained above can be used to help filling saline into a through hole of a catheter (not shown) and installing a guide wire (not shown) into the through hole filled with saline when the catheter is used.

In filling saline into the through hole of the catheter, an end of the catheter is held in the receiving hole, i.e. between the small grooves 21. In this case, the end of the catheter may be inserted into the receiving hole, or the gripping portions 11 may be pushed to open the holding portions 16, and after placing the end of the catheter into the small groove 21, the holding portions may be closed. Since the small grooves 21 have the steps 22, the tip of the catheter with different size can be held in the small grooves 21.

Thereafter, a needle attached to a syringe with saline therein is inserted into the through hole of the catheter through the hollow portion formed by the large grooves 18 greater in diameter than the through hole of the catheter. Then, saline is injected into the through hole of the catheter by the syringe. Since the needle can be easily inserted into the through hole of the catheter through the large grooves 18, saline can be easily supplied to the through hole of the catheter.

After saline is filled in the through hole of the catheter, a guide wire is inserted into the through hole of the catheter. Thus, after filling saline into the through hole, the needle with the syringe is removed from the through hole while the installation device 10 is left to be fixed to the catheter. Then, the guide wire is inserted into the through hole through the hollow portion. Since the size of the hollow portion is greater than that of the through hole, the guide wire can be easily inserted into the through hole of the catheter.

After the guide wire is inserted into the catheter, the gripping portions 11 are pushed toward each other to open the holding portions 16. Accordingly, the guide wire installation device can be easily removed laterally from the guide wire and the catheter. Thereafter, the catheter is inserted into the blood vessel along the guide wire as in the regular procedure.

In the present invention, the necessary procedures in using the catheter, i.e. filling saline in the through hole of the catheter and inserting the guide wire into the through hole of the catheter, can be performed easily. The used installation device can be easily removed from the catheter and the guide wire. Also, the long catheter can be kept in a loop shape easily by the installation device.

While the invention has been explained with reference to the specific embodiments of the invention, the explanation is illustrative and the invention is limited only by the appended claims.

What is claimed is:

1. A guide wire installation device for catheter, comprising:

a pair of elongated main sections arranged to face each other, each main section including a gripping portion at one side, and a holding portion at the other side thereof arranged to slightly incline relative to the gripping portion, said holding portion having first and second grooves communicating with each other and extending in a direction to cross a longitudinal direction of the main section, said first groove having a size greater than that of the second groove so that when the holding portions abut against each other, a hollow portion is formed by the first grooves, and a receiving hole communicating with the hollow portion is formed by the second grooves, a connecting portion located between the holding portion and the gripping portion and connecting the elongated main sections together, and means for holding the holding portions to abut against each other formed between the main sections.

2. A guide wire installation device according to claim 1, wherein said first groove has a tapering surface extending to the second groove to form a conical shape when the holding portions abut against each other.

3. A guide wire installation device according to claim 2, wherein said second groove has step portions with different sizes to form different diameter portions when the holding portions abut against each other, the diameters of the different diameter portions gradually increasing in a direction away from the first groove.

4. A guide wire installation device according to claim 3, wherein said means for holding the holding portions is an elongated curved member located between the gripping portions to apply outward pressure to the gripping portions, said main sections, elongated curved member and connecting portion being integrally formed together by resin.

5. A guide wire installation device according to claim 1, wherein said main section further includes a third groove between the holding portion and the connecting portion to form a clip for a catheter when the holding portions abut against each other.

6. A guide wire installation device according to claim 5, wherein each main section further includes a protrusion extending from the holding portion to have the first groove therein, said protrusion having a projection extending outwardly therefrom.

* * * * *